United States Patent [19]
Swanson et al.

[11] Patent Number: 5,411,525
[45] Date of Patent: May 2, 1995

[54] DUAL CAPACITOR BIPHASIC DEFIBRILLATOR WAVEFORM GENERATOR EMPLOYING SELECTIVE CONNECTION OF CAPACITORS FOR EACH PHASE

[75] Inventors: David K. Swanson, Roseville, Minn.; Raymond E. Ideker; Greg Walcott, both of Durham, N.C.

[73] Assignees: Cardiac Pacemakers, Inc., St. Paul, Minn.; Duke University, Durham, N.C.

[21] Appl. No.: 828,136

[22] Filed: Jan. 30, 1992

[51] Int. Cl.$^6$ ............................................. A61N 1/39
[52] U.S. Cl. ......................................... 607/5; 607/74
[58] Field of Search .................... 128/419 D; 607/5, 4, 607/68, 72, 74

[56] References Cited
U.S. PATENT DOCUMENTS

| 3,093,136 | 6/1963 | Lohr | 128/419 D |
| 3,359,984 | 12/1967 | Daniher et al. | 128/419 D |
| 4,321,928 | 3/1982 | Elmqvist | 128/419 PG |
| 4,548,203 | 10/1985 | Tacker, Jr. et al. | 128/419 D |
| 4,576,170 | 3/1986 | Bradley et al. | 128/419 D |
| 4,800,883 | 1/1989 | Winstrom | 128/419 D |
| 4,821,723 | 4/1989 | Baker, Jr. et al. | 128/419 D |
| 4,850,357 | 7/1989 | Bach, Jr. | 128/419 D |
| 4,951,668 | 8/1990 | Reed | 128/419 R |
| 4,953,551 | 9/1990 | Mehra et al. | 128/419 D |
| 5,199,429 | 4/1993 | Kroll et al. | |

FOREIGN PATENT DOCUMENTS

| 0085383 | 6/1965 | France | 128/419 D |
| 0864362 | 4/1961 | United Kingdom | 128/419 D |

OTHER PUBLICATIONS

Wessale et al., "Bipolar Catheter Defibrillation in Dogs Using Trapezoidal Waveforms of Various Tilts," J. Electrocardiology, 13 (4), 1980, pp. 359–366.
Tang et al., "Ventricular Defibrillation Using Biphasic Waveforms: The Importance of Phasic Duration," JACC, vol. 13, No. 1, Jan. 1989, pp. 207–214.
Feeser et al., "Strength-Duration and Probability of Success Curves for Defibrillation With Biphasic Waveforms, Circulation," vol. 82, No. 6, Dec. 1990.

Primary Examiner—William E. Kamm
Assistant Examiner—Kennedy J. Schatzle
Attorney, Agent, or Firm—Peter Forrest

[57] ABSTRACT

An implantable defibrillator/cardioverter which generates a biphasic defibrillation/cardioversion waveform including a pulse generator comprising two capacitors and a pair of switches for connecting the capacitors in parallel during a first phase and in series during a second phase. The first phase has a small "tilt" between the leading edge voltage and the trailing edge voltage. The second phase has a leading edge voltage which is approximately twice the trailing edge voltage of the first phase.

5 Claims, 2 Drawing Sheets

DUAL CAPACITOR BIPHASIC DEFIBRILLATOR WAVEFORM GENERATOR EMPLOYING SELECTIVE CONNECTION OF CAPACITORS FOR EACH PHASE

RELATED APPLICATION

This application is related to U.S. patent application Ser. No. 07/827,215, filed on the same day as this application, and entitled "DEFIBRILLATOR WAVEFORM GENERATOR FOR GENERATING WAVEFORM OF LONG DURATION".

BACKGROUND OF THE INVENTION

The present invention relates to cardiac defibrillation/cardioversion, and more particularly to an implantable defibrillation/cardioversion system including a pulse generator which generates a lower energy biphasic defibrillation/cardioversion waveform.

When used hereinafter, the term "defibrillation" is meant to include high energy defibrillation and lower energy cardioversion.

Biphasic internal defibrillation has replaced monophasic defibrillation as a technique to decrease defibrillation strength requirements. See, for example, U.S. Pat. Nos. 4,548,203 to Tacker, Jr. et al. and 4,821,723 and 4,850,357 to Bach, Jr. By decreasing defibrillation strength requirements, the energy storage devices in the implanted unit can be smaller.

With the desire to minimize energy requirements in implanted devices, there is room for improving biphasic defibrillation.

SUMMARY OF THE INVENTION

It is a primary object of the present invention to provide a defibrillator which is capable of generating an effective defibrillation waveform with less of electrical energy.

It is another object of the present invention to provide an implantable defibrillator which defibrillates the heart with lower peak voltages.

It is yet another object of the present invention to provide an implantable defibrillator which defibrillates the heart with a biphasic waveform comprising a low tilt, long duration first phase (8–30 ms) having lower peak voltages than presently available defibrillators.

It is still another object of the present invention to provide a pulse generator for an implantable defibrillator including first and second capacitors, the first and second capacitors being connected in parallel during a first phase and in series during a second phase, to generate a biphasic waveform.

It is yet another object of the present invention to provide an implantable defibrillator which defibrillates with lower peak voltages so as to minimize tissue both tissue stunning and post-shock depression of local electrograms.

Yet another object of the present invention is to reduce the amount of unused energy of the capacitors in generating a biphasic defibrillation waveform.

The present invention relates to a pulse generator for an implantable defibrillator (or cardioverter) which generates a biphasic defibrillation waveform with reduced energy requirements. The pulse generator comprises two capacitors and a pair of switches for connecting the capacitors in parallel during a first phase and in series during a second phase. The first phase has a small "tilt" between the leading edge voltage and the trailing edge voltage. "Tilt" refers generally to a capacitor's rate of charge or discharge. Tilt is graphically represented as a line or slope to indicate an amount of electrical charge or discharge per unit of time. The second phase has a leading edge voltage which is approximately twice the trailing edge voltage of the first phase. By delivering higher peak voltages during the lower capacitance second phase, the peak voltages of the first phase can be lowered. Further still, by lower peak voltages, tissue stunning is minimized.

The aspects of the present invention, while particularly useful in implantable systems, are also applicable in external defibrillation systems.

The above and other objects and advantages will become more readily apparent when reference is made to the following description taken in conjunction with the accompanying drawings.

DETAILED DESCRIPTION OF THE DRAWINGS

Figure 1:
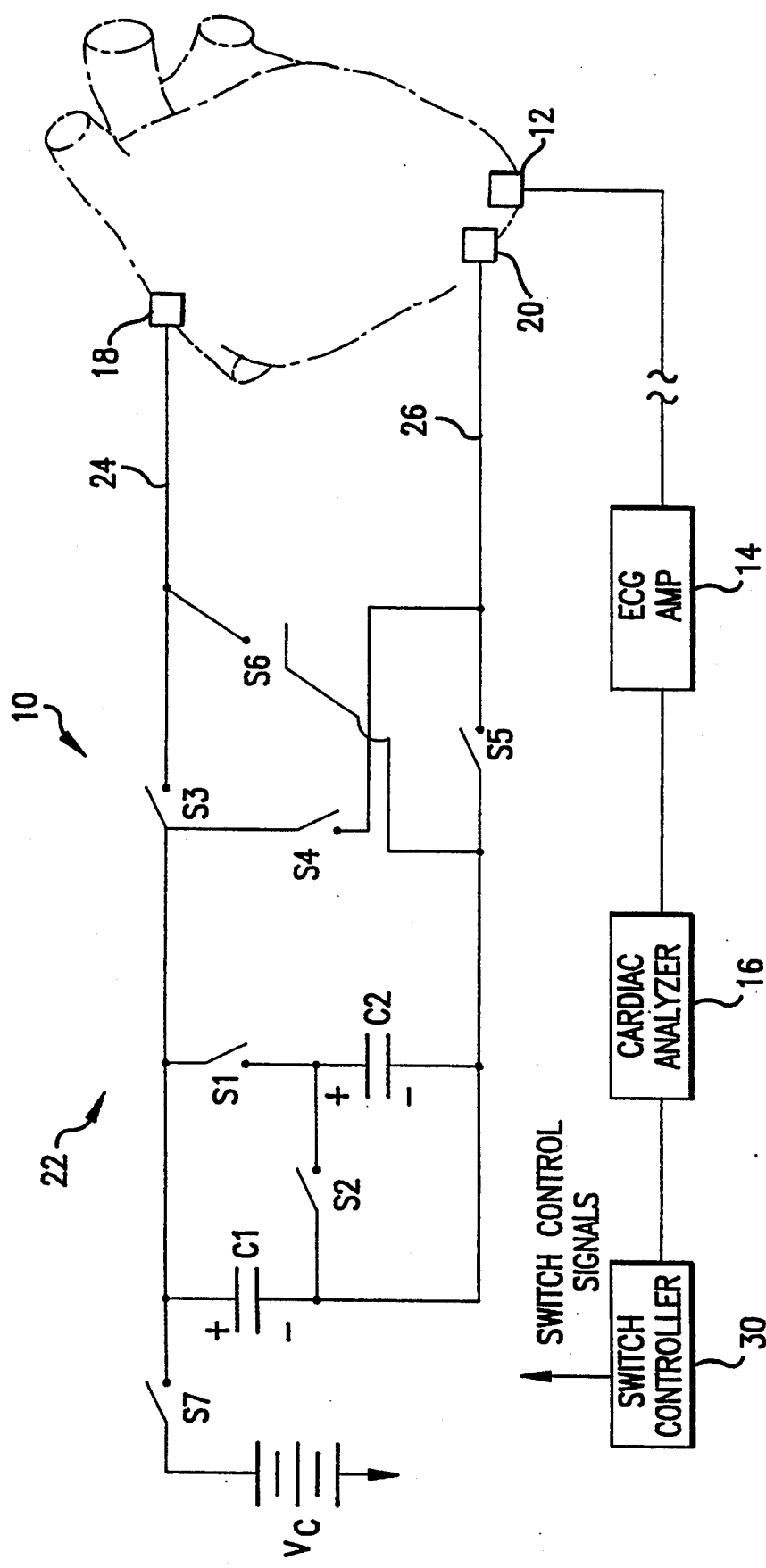
FIG. 1 is a schematic diagram illustrating the implantable defibrillation system according to the present invention.

FIG. 1 illustrates the defibrillation system according to the present invention, which is generally shown at 10. The system 10 includes a sensing electrodes 12 and circuitry for amplifying and analyzing the cardiac rhythm, in the form of an ECG amplifier 14 and a cardiac analyzer 16. The cardiac analyzer 16 determines when the heart is in a condition requiring a defibrillation ( or cardioversion shock) and issues a control signal, causing the shock to be delivered to the heart via electrodes 18 and 20. The shock is a biphasic waveform having first and second phases. The first phase is generated by discharging a first capacitance and the second phase is generated by discharging a second capacitance. The first capacitance is greater than the second capacitance. The first phase is accordingly of substantially smaller tilt than the second phase.

The thrust of the present invention lies in the pulse generator circuitry, which is generally shown at 22. The pulse generator circuitry includes capacitors C1 and C2 connected to each other, either in series or in parallel, by switches S1 and S2. The capacitors C1 and C2 are charged by the voltage supply Vc, and are connected to the electrodes 18 and 20 via lead lines 24 and 26. A plurality of switches S3–S6 are provided between the capacitors C1 and C2 and the lead lines 24 and 26. Preferably, capacitors C1 and C2 are about 350 microFarads each.

A switch controller 30 is provided to control the switches S1–S6. Switches S1–S6 thereby control the discharge waveform of the capacitors C1 and C2. In general, the switch controller 30 controls the switches so that a biphasic waveform is generated from the discharge of the capacitors C1 and C2, with the capacitors C1 and C2 being connected in parallel during the first phase, and in series during the second phase. This is done so that the first phase of the biphasic waveform has a low tilt, thus allowing for a decrease in the peak voltage during the first phase.

Figure 2:
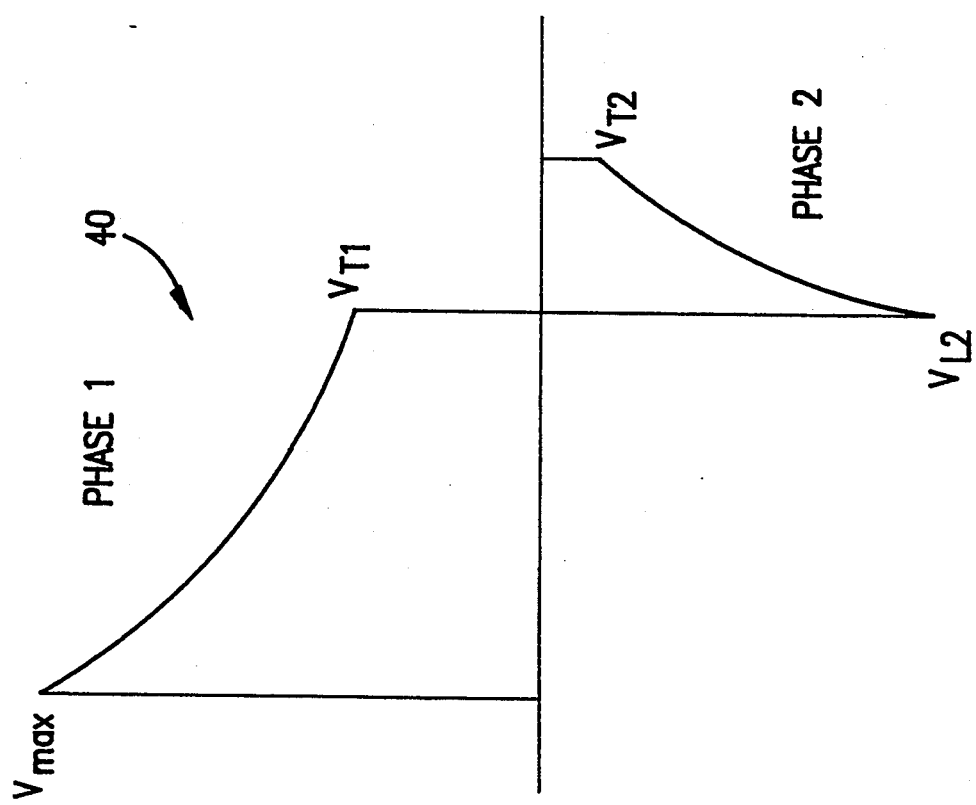
FIG. 2 is a diagram of a biphasic waveform generated by the pulse generator of the implantable defibrillation system according to the present invention.

With additional reference to FIG. 2, the method by which the biphasic waveform 40 is generated will be described. The capacitors C1 and C2 are charged via the voltage supply Vc, by closing the switch S7. This may be controlled by the switch controller 30, or the cardiac analyzer directly 16. Once charged, the switch controller generates phase 1 of the waveform by closing switch S1 and moving switch S2 from position B to position A. This connects the capacitors C1 and C2 in parallel. Just prior to this, switches S3 and S5 are closed and switches S4 and S6 are opened, so that the first phase is of positive polarity. The overall capacitance for the first phase is, therefore, the sum of the capacitance of capacitors and C2, which is 700 microFarads. Consequently, the discharge waveform for phase 1 will slowly decay from a leading edge voltage VL1 to a trailing edge voltage VT1. The decay from VL1 to VT1 will be slow because the time constant for the circuit will be large, due to the sum of the capacitances of capacitors C1 and C2. Furthermore, as a result, the "tilt" of the first phase will be quite small, because the difference between the leading edge voltage VL1 and the trailing edge voltage VT1 is small.

For the second phase of the waveform, the switch controller 30 opens switch S1 and closes switch S2 from position A to position B, thereby connecting capacitors C1 and C2 in series. In addition, switches S4 and S6 are closed and switches S3 and S5 are opened, so that phase 2 is of opposite polarity from phase 1. The overall capacitance for the discharge waveform of phase 2 is the series combination of capacitors C1 and C2 (175 microFarads), which is approximately four times less than the parallel combination of phase 1. The discharge waveform for phase 2, therefore, decays about four times faster than phase 1 from the leading edge voltage VL2 to the trailing edge voltage VT2. Furthermore, the leading edge voltage of phase 2, VL2, is twice the trailing edge voltage VT1 of phase 1.

The biphasic waveform of the present invention has several advantages over known defibrillation waveforms. First, by lengthening the duration of the first phase and causing the tilt of this phase to be small, the peak voltage for the leading edge of the first phase, VL1, can be decreased, thus minimizing energy requirements and improving the efficiency of energy stored in the capacitors. On the other hand, by decreasing the capacitance for the second phase, the second phase delivers the remaining energy stored in the capacitors at a higher leading edge voltage, without requiring additional energy. Moreover, it has been found through experimental testing in animals that the biphasic waveform of the present invention defibrillates at a significantly lower phase 1 leading edge voltages and total stored energy than biphasic waveforms heretofore known.

An even further advantage of lengthening the duration of the first phase is that peak voltages can be decreased overall. Consequently, tissue damage caused by the trailing edge voltage of the first phase can be minimized, and post-shock sensing of the heart is thereby improved.

Yet a further consequence of the defibrillation waveform according to the present invention is that more of the energy stored in the capacitors is used in generating the waveform, increasing the efficiency of the pulse generator.

An alternative method to generate the biphasic waveform according to the present invention comprises partially discharging a first capacitor, then discharging a second capacitor, to generate a first phase. For the second phase, the polarity is reversed and the first and second capacitors are connected in series and discharged.

The foregoing description is intended by way of example only and is not intended to limit the present invention in any way except as set forth in the following claims.

We claim:

1. A pulse generator for generating a defibrillation waveform in a defibrillator for discharge between at least two electrodes implanted on or about the heart, said pulse generator comprising:
   a first capacitor;
   a second capacitor;
   first switch means for connecting the first capacitor and second capacitor in series or in parallel;
   lead lines for connecting the first and second capacitors to said at least two electrodes;
   means for charging said first and second capacitors;
   second switch means for connecting said first and second capacitors to said lead lines; and
   switch control means for controlling said first and second switch means to connect said first and second capacitors in parallel for discharge via said at least two electrodes for a first phase of a biphasic waveform, and to connect said first and second capacitors in series for a second phase of said biphasic waveform.

2. The pulse generator of claim 1, wherein said switch control means controls said second switch means to connect said first and second capacitors to said lead lines so that said first phase is of positive polarity and so that said second phase is of negative polarity.

3. A method for generating a defibrillation waveform in an implantable defibrillator for discharge between at least two electrodes implanted on or about the heart, said method comprising the steps of:
   providing first and second capacitors;
   connecting with a first Switch means said first and second capacitors in parallel;
   discharging said first and second capacitors connected in parallel to generate a first phase of a biphasic waveform;
   connecting with a second switch means said first and second capacitors in series and in reverse polarity at the end of the first phase; and
   discharging said first and second capacitors connected in series to generate a second phase of a biphasic waveform.

4. A method for generating a biphasic defibrillation waveform comprising the steps of:
   generating from a first capacitor and a second capacitor connected in parallel by a first switch means a first phase having a predetermined tilt between a leading edge voltage and a trailing edge voltage; and
   generating from the first capacitor and the second capacitor connected in series by a second switch means a second phase having a leading edge voltage approximately twice that of the trailing edge voltage of the first phase.

5. An implantable defibrillation/cardioversion system comprising:
   at least two implanted defibrillation/cardioversion electrodes;

a pulse generator connected to the electrodes for generating a defibrillation waveform in an implantable defibrillator/cardioverter for discharge between said at least two electrodes implanted on or about the heart, said pulse generator comprising:

a first capacitor;

a second capacitor;

first switch means for connecting the first capacitor and second capacitor in series or in parallel;

means for charging said first and second capacitors;

second switch means for connecting said first and second capacitors to lead lines connecting to said at least two electrodes; and switch control means for controlling said first and second switch means to connect said first and second capacitors in parallel for discharge via said at least two electrode for a first phase of a biphasic waveform, and to connect said first and second capacitors in series for a second phase of said biphasic waveform.

* * * * *